(12) United States Patent
Kiontke

(10) Patent No.: US 6,425,851 B1
(45) Date of Patent: Jul. 30, 2002

(54) DEVICE AND PROCESS FOR ACTIVATING OBJECTS

(76) Inventor: Siegfried Kiontke, Gustav-Metrink-Strasse 6, Munich (DE), D-81245

( * ) Notice: Subject to any disclaimer, the term of this patent is extended or adjusted under 35 U.S.C. 154(b) by 0 days.

(21) Appl. No.: 09/530,087

(22) PCT Filed: Oct. 22, 1998

(86) PCT No.: PCT/EP98/06723

§ 371 (c)(1),
(2), (4) Date: Aug. 17, 2000

(87) PCT Pub. No.: WO99/21614

PCT Pub. Date: May 6, 1999

(30) Foreign Application Priority Data

Oct. 23, 1997 (DE) .......................................... 197 46 791
Nov. 28, 1997 (DE) .......................................... 197 52 934

(51) Int. Cl.[7] .............................. A61N 2/00; A61N 1/08
(52) U.S. Cl. ............................................. 600/9; 607/60
(58) Field of Search ................... 600/13, 409; 128/897; 606/13; 435/173.5, 285.2, 173.1

(56) References Cited

U.S. PATENT DOCUMENTS

| | | | | |
|---|---|---|---|---|
| 3,557,777 A | * | 1/1971 | Cohen | ........................ 600/409 |
| 4,818,697 A | * | 4/1989 | Liboff et al. | .............. 435/173.5 |
| 4,932,951 A | * | 6/1990 | Liboff et al. | .................. 606/13 |
| 5,100,373 A | * | 3/1992 | Liboff et al. | .................. 600/13 |
| 5,106,361 A | * | 4/1992 | Liboff et al. | .................. 600/13 |
| 5,312,534 A | * | 5/1994 | Liboff et al. | .............. 435/285.2 |
| 5,450,859 A | * | 9/1995 | Litovitz | ...................... 128/897 |
| 5,919,679 A | * | 7/1999 | Blackman et al. | ....... 435/173.1 |
| 5,997,464 A | * | 12/1999 | Blackwell | .................... 600/13 |

* cited by examiner

Primary Examiner—Eric F. Winakur
Assistant Examiner—Nikita R Veniaminov
(74) Attorney, Agent, or Firm—O'Melveny & Myers LLP

(57) ABSTRACT

A device and process are provided for activating objects, i.e., substances, organic and inorganic materials or living plant, animal or human bodies and parts thereof, which takes into account the effect of the Earth's magnetic field. An object to be activated is screened from external magnetic fields, such as the Earth's magnetic field or artificial magnetic fields caused by electrical equipment and subjected to a defined constant or variable magnetic field. Activation then takes place by defining a magnetic environment in the spatial region of the object. The weak magnetic field produced by the device may be constant, or may be changed with time since a human body also moves in the Earth's field and is therefore subjected to different field values and field directions.

32 Claims, 4 Drawing Sheets

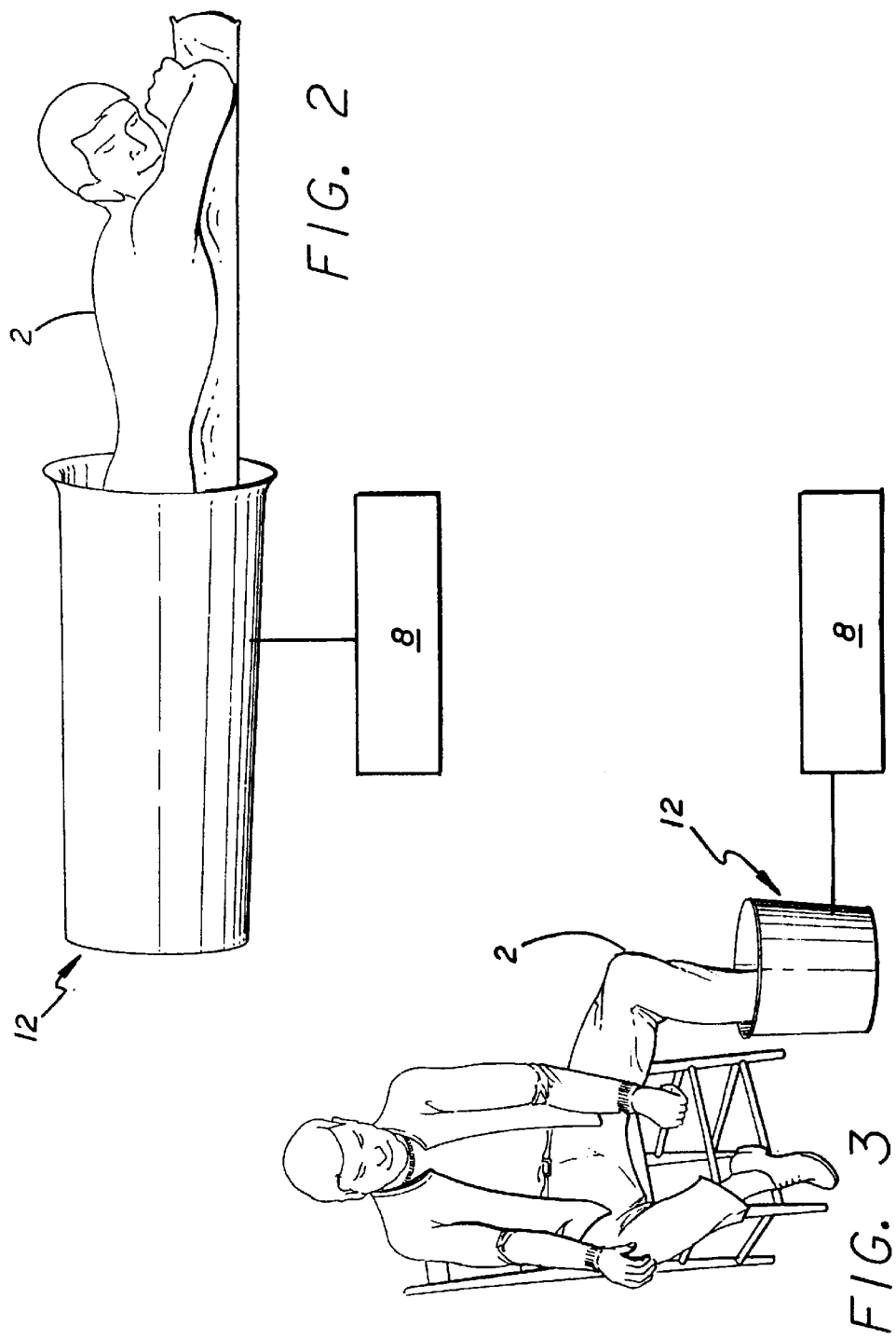

DEVICE AND PROCESS FOR ACTIVATING OBJECTS

FIELD OF THE INVENTION

The invention relates to a device for activating objects in the form of substances, organic materials or living plant, animal or human bodies and parts thereof and a process for activating objects in the form of substances, organic materials or living plant bodies and parts thereof.

BACKGROUND OF THE INVENTION

From the beginning of this century, the question of whether electromagnetic radiation can be emitted by organisms and whether the function of cells is affected by this has been a matter of discussion. In the seventies, F. A. Popp first provided experimental evidence that cells do emit biologically significant photon radiation. It is assumed that the frequency range of this radiation extends from very small values of less than 1 Hz up to very large values of more than $10^{18}$ Hz. It is assumed that the body has its own energy field of an electromagnetic nature and that this electromagnetic field takes precedence over biochemical control and regulation processes. Thus, a disease is indicated by a change at the superordinate electromagnetic control level. Such pathological changes are also called interference vibrations which have an effect on the natural magnetic field of the body and can trigger faulty regulation processes.

Using these principles, a therapy device has been produced which works with the so-called endogenous vibrations for a body or a substance and by means of which an improvement or cure can be produced by extinguishing the interfering vibrational pattern. In this process, using modern electronics, the vibration pattern from human or animal bodies or from plants or even the characteristic electromagnetic fields of other organic and inorganic substances are processed via a bioresonance therapy instrument and applied to the organism for healing purposes. This makes use of the possibility of attenuating or amplifying the signals picked up by reception antennae from bodies or substances and also of inverting the signals in order to extinguish false, pathological electromagnetic vibrations or to stimulate or amplify correct, physiological electromagnetic vibrations in the patient by resonance or extinguishing effects.

With bioresonance therapy, therefore, substantially the following prerequisites are used as the starting point: the body and the biochemical processes in the body are electromagnetically controlled, i.e. there are electromagnetic vibrations in and around the body. These take precedence over biochemical processes and control them so that a vibrational spectrum of the organism is produced. In addition to physiological vibrations, there are also pathological vibrations in every person, these being caused by toxic pollution, injuries, infections, non-cured diseases, allergies, etc. Corresponding vibrations are present in substances. The endogenous electromagnetic fields in bodies or substances can be picked up from the surface and processed in a therapy instrument. Therapy vibrations are produced in the therapy instrument from these vibrations and these are passed to the body. The therapy vibrations cause a therapeutic effect in the body of the patient by extinguishing or reducing pathological vibrations or stimulating or amplifying physiological vibrations.

The improvement in the biophysical energy situation thus leads to effective therapy. This form of therapy has been known for twenty years, wherein the term Mora® therapy was that first used and the term bioresonance has now become widely accepted. Reference is made, in general, to the techniques of bioresonance therapy in the relevant literature, for example the publications by F. Morell in Ganzheitsmedizin volume 0/4-87, page 17 and by W. Ludwig, 'Die Grundlagen der Bioresonanz-Therapie', from Bioresonanz-und Multiresonanz-Therapie, Haug Verlag 1990. Other publications relating to bioresonance therapy have been published by the Brügemann Institute in Cauting, for example the publication by H. Brügemann, 'Bioresonanz-Therapie—Grundlagen und Praxis', on the further development of therapy using the patient's endogenous vibrations, and the publication by P. Schumacher, 'Allergie aus biophysikalischer Sicht'.

Any substance, whether inorganic or organic, emits an electromagnetic vibrational pattern which lies in both the low and high frequency regions. The physical description of the electromagnetic emissions from substances in the long-wave region can be found by means of the Rayleigh-Jeans Law. The radiation curve for a black body at a temperature of 300 K has a maximum at 10 $\mu$m, that is in the IR region. However, there is also low frequency radiation according to the radiation law. Thus, radiation of about 8700 photons per $cm^2$ per second would be expected to be emitted e.g. between 0.9 and 1.1 MHz. These values have to be modified for a real body as compared with black body radiation. In fact, the varying spectral emissions of different materials can be explained as deviations from hypothetical black body radiation.

In the case of organic substances, there is an additional source of radiation which does not apply to inorganic materials, biophoton radiation. The physicist Dr. Popp has recorded remarkable spectra in the UV region, by using photomultipliers which can detect this type of radiation. According to the physicist Bigu del Blanco the spectrum for humans is very wide-band in structure. Although it has not yet been measured, it is assumed that similar spectra are also present for animals and plants. Also, biophotons, which are emitted by living substances, should have the low frequency modulation mentioned above.

The radiation which is characteristic of any substance, which exists in both the low and high frequency region, can be received by an input antenna and processed with an electronic circuit e.g. amplified, inverted or attenuated. By means of a transmitter antenna, this processed signal can be sent to a carrier substance which can store this vibrational pattern, or can be transferred to a body. Transferring is the normal expression for the handing over of a signal. The transmitter substance can be a natural or artificial preparation or one of the body's own substances. Transfer to a body represents a therapeutic application.

DE-OS 31 10 915, DE-OS 30 27 621 and DE-OS 32 44 582 make known an arrangement by means of which the human body can be subjected to a varying or modulated magnetic field. Also, in the case of the vibrational-magnetic field therapy unit known from DE-OS 41 35 325, an ampoule with a paramagnetic reagent is subjected to a magnetic field and activated in this way.

The MitoSan system is produced and marketed by the Vitatec GmbH medical engineering products Co., and objects which are to be treated or activated are subjected to a weak and varying magnetic field in this system. In addition, vibrations in the region of ultraweak electromagnetic signals can also be produced with the MitoSan system. These ultraweak signals correspond, under physiological conditions and in the context of the genetic control system, to those of the cells themselves. If these ultraweak signals are missing in patients, the organism is stimulated by the application of the vibrational pattern of MitoSan therapy to build them up again; the diseased cell system can then regenerate itself.

These known irradiation instruments are used in the natural medicine sector for the transfer of vibrations from medicaments, e.g. homeopathic agents and from samples of test substances which are used to test for allergies or substance incompatibilities, to carrier substances or patients using electromagnetic or magnetic waves. The phenomenon of homeopathy has been now been studied in earnest and it is a possible explanation of the mode of action of homeopathic or similar agents that electromagnetic signals of extremely weak intensity are transferred to biological organisms. In this case it seems that the possibility that water can store electromagnetic information in its cluster structures plays an important role.

The disadvantage of known therapy instruments or devices for irradiating and activating objects is that the effect of the Earth's magnetic field, which varies with time and locality, is not taken into account.

Therefore, the object of the present invention is to provide a device and a process for activating objects, i.e. substances, organic and inorganic materials or living plant, animal or human bodies and parts thereof which takes into account the effect of the Earth's magnetic field.

SUMMARY OF THE INVENTION

In the context of the invention, it was found that the Earth's magnetic field has an effect on the activation of objects. The effect of magnetic fields on objects to be activated can be explained in that the movements of charged particles such as ions, charged molecules, atomic nuclei or electrons are affected by a magnetic field. Energy can be transferred to charged particles with the aid of a magnetic field and this has an effect on their orbital motion.

In the case of irradiation, activation of substances which are located in a magnetic field with a suitable frequency, the resonance frequency, the substances to be activated take up energy by means of a resonance effect, and this is then given out again by emitting electromagnetic radiation. The emitted radiation in this case is then characteristic of the substance for a given static magnetic field. These resonance effects are:

nuclear magnetic resonance (NMR)
electron spin resonance (ESR)
cyclotron resonance The physical principles of these resonance effects can be found in relevant physics textbooks, so no details have to be given here. Reference is also made here to an article by the inventor in 'Zeitschrift für medizinische Regulationsdiagnostik und-therapies', vol. 3, September 1998, pages 67 to 73, with the title "Resonazphänomene und die Änderung von Stoffabstrahlung".

With regard to the fact that the body is subjected to the Earth's magnetic field, the strength of which is on average between 20 T and 60 T, it would therefore be expected that the magnetic field would have an effect on disturbances in the body. The Earth's magnetic field combines with any electromagnetic fields of terrestrial or extraterrestrial origin and triggers the resonance phenomena explained above. Since disturbances in the body can occur at a specific point in time with a certain magnetic field and a certain electromagnetic field, it can be seen that suitable conditions have to be set up in order to alleviate the stored disturbances.

So that the Earth's magnetic field, which is also a weak magnetic field, can be screened from the object to be activated, the effect of the Earth's magnetic field has to be eliminated. Screening of the magnetic field takes place in the region of the object to be activated, i.e. the spatial area in which the object to be activated is located is screened. Screening of the Earth's magnetic field may then take place passively, e.g. via a material with a high permeability ($\mu$-metal, soft iron), or actively, i.e. by means of an artificially produced magnetic field with the opposite polarity. Screening is designed in such a way that, in the spatial region in which the object to be activated is located, the Earth's magnetic field and also external artificial magnetic fields not produced by the device according to the invention itself, are screened.

A defined magnetic environment is then created in the spatial region of the object to be activated, so that it is possible to produce specific magnetic conditions which have the desired activating or therapeutic effect. The weak magnetic field produced by the device according to the invention may in principle be constant, i.e. it can be variably adjusted to a fixed value. Preferably, however, the strength and/or direction of the magnetic field can be changed with time since a human body also moves in the Earth's field and is therefore subjected to different field values and field directions.

The Earth's magnetic field is subject to periodic variations which are repeated with a period of 13 hours at a frequency of up to 22 kHz. The higher the frequency, the smaller the change in field strength. The Earth's magnetic field and in particular the changes in the Earth's magnetic field can be artificially reproduced with the device according to the invention, wherein overlapping of the artificially produced "Earth's magnetic field" and the natural Earth's magnetic field by screening can be avoided. Due to the preferably automatic changes in the magnetic field, all relevant magnetic fields can thus be defined without passing through an overlap with external magnetic fields, so that a precisely adjusted signal is produced in every case. It has been shown that reproduction of the temporal changes in the natural Earth's magnetic field with higher or lower field strengths than the natural magnetic field is particularly beneficial for the activation of substances and is also more therapeutically effective than identical reproduction of the Earth's magnetic field.

If temporal variation of the artificially produced magnetic field takes place with not too high a frequency, for example with a frequency of less than 10 Hz, wherein in practice also slow changing of the magnetic field over a period of about 30 sec may be advantageous, it can be regarded as a quasi-static magnetic field with regard to the much shorter time constants which play a part in the processes in the substance to be activated.

In the simplest case, the object to be activated is screened from external magnetic fields, such as the Earth's magnetic field or artificial magnetic fields caused by electrical equipment and subjected to a defined constant or variable magnetic field. Activation then takes place due to the combined effects of the weak magnetic field and the terrestrial and extraterrestrial radiation which is present, and which is not screened by magnetic screening.

Due to the screening of all external magnetic fields, if possible to a value of zero, and subsequent controlled variation in the magnetic field applied with a certain rhythm or else at a fixed, selectable, value, it is possible to subject the object to be activated, e.g. the human body, to a magnetic field which acts in an optimal manner for it in the particular situation and with stimulation by artificial and/or natural broad-band spectra and it can thereby experience increased bodily well-being. This takes place on the one hand due to the artificially produced "appropriate" magnetic field and on the other hand due to the resonance effect associated with this magnetic field in the form of NMR, ESR and cyclotron resonance spectra.

According to one advantageous variant of the invention, activation also takes place by means of thermal, electromagnetic, electrical, optical or magnetic excitation. The activating agent then includes an activation antenna arranged in the region of the object to be activated. This activating agent can be affected and modulated in a targeted manner in contrast to the environmental radiation which is present.

According to an advantageous variant of the invention, a vibrational pattern is derived from a radiating transmitter substance or the object to be activated, by means of a reception antenna, the signal is processed in a processing unit and is transferred to the carrier substance via a transmitter antenna.

The solution according to the invention is based on the knowledge that it is possible to thermally, electromagnetically, electrically or magnetically excite the transmitter substance or the substance to be activated by means of an activating agent, which means the therapy signal picked up by means of the reception antenna is stronger than the signal present without activation or the signal is produced with the amplitude or frequency for the particular application. In this way, the signal intensity of a substance whose original emission of radiation has declined or been lost, can be excited again and can be used for the purposes described. In the case of transmitter substances which still have their normal radiation emission intensity, the radiation emission can be intensified by activation according to the invention. It is assumed from this that in the case of purely inorganic substances a substantial amplification effect occurs since their emission radiation decreases only very slowly with time. In other cases a "suitable" signal can be provided.

A variety of activating agents are suitable for activating a transmitter substance, i.e. to supply suitable energy, in particular in the form of vibrations. According to a first preferred feature, it is suggested that the activating agent includes an activation antenna. Using an activation antenna, electromagnetic vibrations are transferred to the transmitter or to the object to be activated, wherein the frequencies or the polarity can be adjusted in a desired manner.

For optimal excitation of low frequency vibrations, it is preferable that the radiation instrument includes both a magnetic activating agent, that is a device for producing a magnetic field at the location of the transmitter substance or the object to be activated and also a thermal or electromagnetic activating agent. By a combination of these measures, intense activation can be achieved, in particular at low frequencies. If a delay circuit is also used, then the signal can be affected in a manner which is the optimum for the effect to be produced. Storage of the signal is also possible in this case.

Another advantageous activating agent may be a light source. All types of lamps and light sources, which emit continuously or intermittently, are suitable for this purpose, in particular flash bulbs, miniaturised lasers and IR diodes.

Another advantageous activating agent may comprise a source of heat. This may be, for example, a source of radiant heat or a heating resistance placed in contact with the transmitter substance or its container.

In many cases it may be advantageous to use two or more identical or different activating agents (e.g. activation antenna, source of light and source of heat) in combination.

In order to produce optimum activation, according to a preferred feature, it may be arranged that the control unit or the activating agent be designed to emit a number of frequencies by means of the activating agent. In the context of the invention, it was found that broad-band excitations are particularly effective. It is most advantageous therefore if the widest possible spectrum of frequencies acts on the transmitter substance for activation purposes. The action may then be constant or may vary with time. However it is also advantageous when a varying frequency, e.g. from frequency generator, is used to produce activation encompassing many frequencies. The frequencies may lie between a few Hertz and 30 GHz.

According to another advantageous feature, it may be arranged that the activating agent be activatable periodically or aperiodically in pulses. It has been found that activation which is not performed in a permanent manner, but has relaxation pauses for the transmitter substrate in between activating pulses, is especially advantageous in many areas of application. Furthermore, it may be advantageous, especially in the case of electromagnetic activation using a transmitter antenna, if there are activation pauses present in which the physiological electromagnetic signal can be picked up by the transmitter substance by means of the reception antenna without being overlaid by an interference signal from the activating agent, i.e. the activation antenna.

A preferred further development may consist of the activating agent emitting in one of the two atmospheric windows and/or being pulsed with a frequency in one of the two atmospheric windows. This can be explained on the following basis.

Life on Earth has developed in a wide spectrum of electromagnetic signals with very different intensities. The property of the atmosphere to transmit certain electromagnetic frequencies better than others and to weaken others to almost zero is critical here. There are two so-called "atmospheric windows". The first is the optical window and includes the visible region of the electromagnetic spectrum. This window has been used by organisms in order to develop the ability to see. The limiting regions are also important for life; the UV region for example for synthesising vitamin D and the IR region for heat. The second atmospheric region includes the electromagnetic region from 3 MHz to 30 GHz.

In the context of the invention, it has been confirmed that it is advantageous for the activation of transmitter substances or objects if broad-band, naturally occurring spectra from a few Hertz up to several GHz are used, and in particular if the frequencies lie within the atmospheric windows. An advantageous agreement with or approximation to naturally occurring spectra is produced in this way.

According to a further preferred feature, it is suggested that the activating agent be activatable in a pulsed manner using a pulse frequency between 7 and 9 Hz, preferably about 7.8 Hz. This aspect in accordance with the invention is based on the following knowledge. Mankind and his environment are located in a kind of cavity resonator which has an effect on and occasionally controls the organism. The cavity resonator for its part is produced on the one side by the surface of the Earth and on the other side by the Heaviside layer of the atmosphere. As a result of weather activity and other atmospheric phenomena, this cavity resonator is excited to produce vibrations, wherein the fundamental frequency of the wave vibrations is at about 7.8 Hz and wherein the waves are called the "Schumann waves". It has been found that this frequency of 7.8 Hz is the same as the hippocampus frequency, this being largely the same in all mammals. Humans require the Schumann resonances as a biotropic stimulus and if it is missing this may be expressed in a variety of disorders. The Schumann waves, which may have varying frequencies, are pulsed incidents which are composed of the fundamental and harmonic frequencies. The nervous system responds to both the fundamental and also the harmonic frequencies. This also applies to objects to be activated.

For this reason, it is understandable why a broad-band spectrum from a few Hertz up to the GHz region with a repeating frequency of about 7.8 Hz corresponding to the Schumann waves is advantageous.

An additional advantageous feature consists in including a delay circuit in the signal processing step by means of which the output signals can be time-delayed with respect to the input signals. This feature is based on the surprising finding that substances, organs and other body systems can not only be treated in specific frequency regions, but that the time relationship between the input signal picked up by the transmitter substance and the output signal acting on the body or carrier substance is of critical importance.

In an advantageous manner, the phase position of the signals received by the reception antenna can also be changed to that of the signals radiated by the transmitter antenna, using the processing unit, as is known from German Utility Model D 29709094.1. Thus, reference is made here to this Utility model in its entirety.

BRIEF DESCRIPTION OF THE FIGURES

Further details, features and advantages of the invention are also given in the following description of preferred embodiments, using the drawings. These show:

FIG. 2 a schematic representation of a second embodiment of the invention;

FIG. 3 a schematic representation of a third embodiment of the invention;

DETAILED DESCRIPTION OF THE PREFERRED EMBODIMENT

Figure 1:
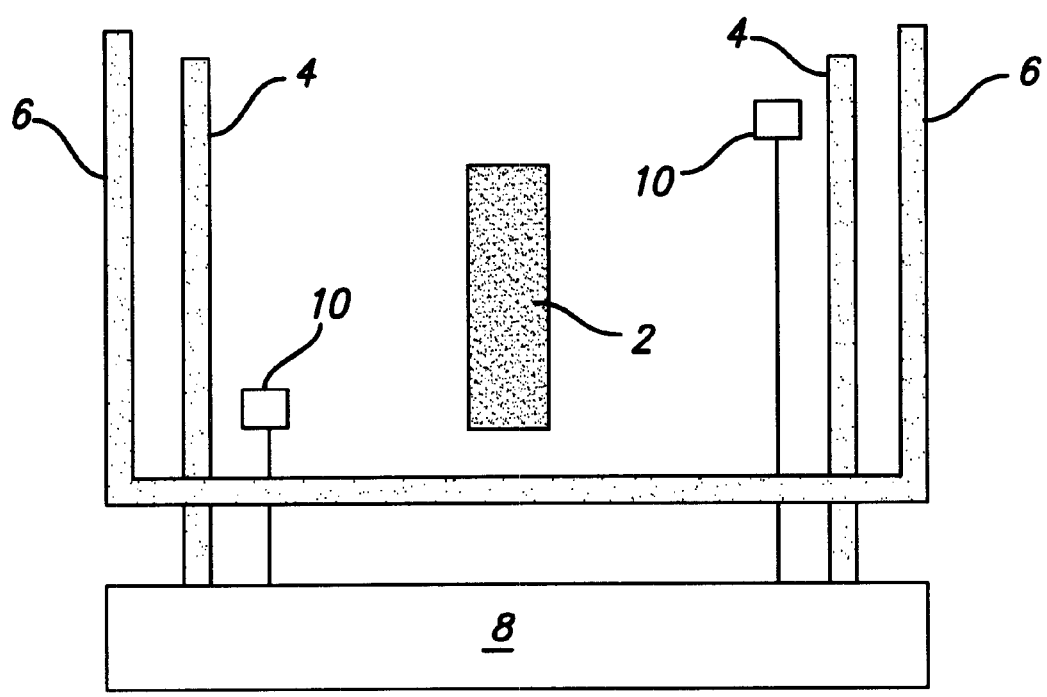
FIG. 1 a schematic representation of a first embodiment of the invention.

FIG. 1 is a representation of a first embodiment of the invention. An object 2 to be activated is arranged inside a magnetic field coil 4. The magnetic field coil 4 is in turn arranged inside passive magnetic screening 6. The magnetic field coil 4 is controlled by a control unit 8. The magnetic field coil 4 is used both to produce a weak magnetic field as an activating agent and also to produce a screening polarised magnetic field which compensates for the Earth's magnetic field and any other external magnetic fields. In order to achieve this active magnetic screening, magnetic field sensors 10 are located inside the magnetic field coil 4 in the region of the object to be activated. These magnetic field sensors provide a controlled quantity for the magnetic field to be regulated inside the magnetic field coil 4.

FIGS. 2 and 3 show a second and third embodiment of the invention which is suitable for treating the human body or parts thereof. A tubular housing 12 contains the magnetic field coil, screening and magnetic field sensors, which are not shown in detail, which are controlled by control unit 8. In the second embodiment according to FIG. 2, the housing 12 is large enough to take a human body. In the third embodiment according to FIG. 3, the housing 12 is smaller and is used simply for taking a foot, a hand or the like.

Figure 4:
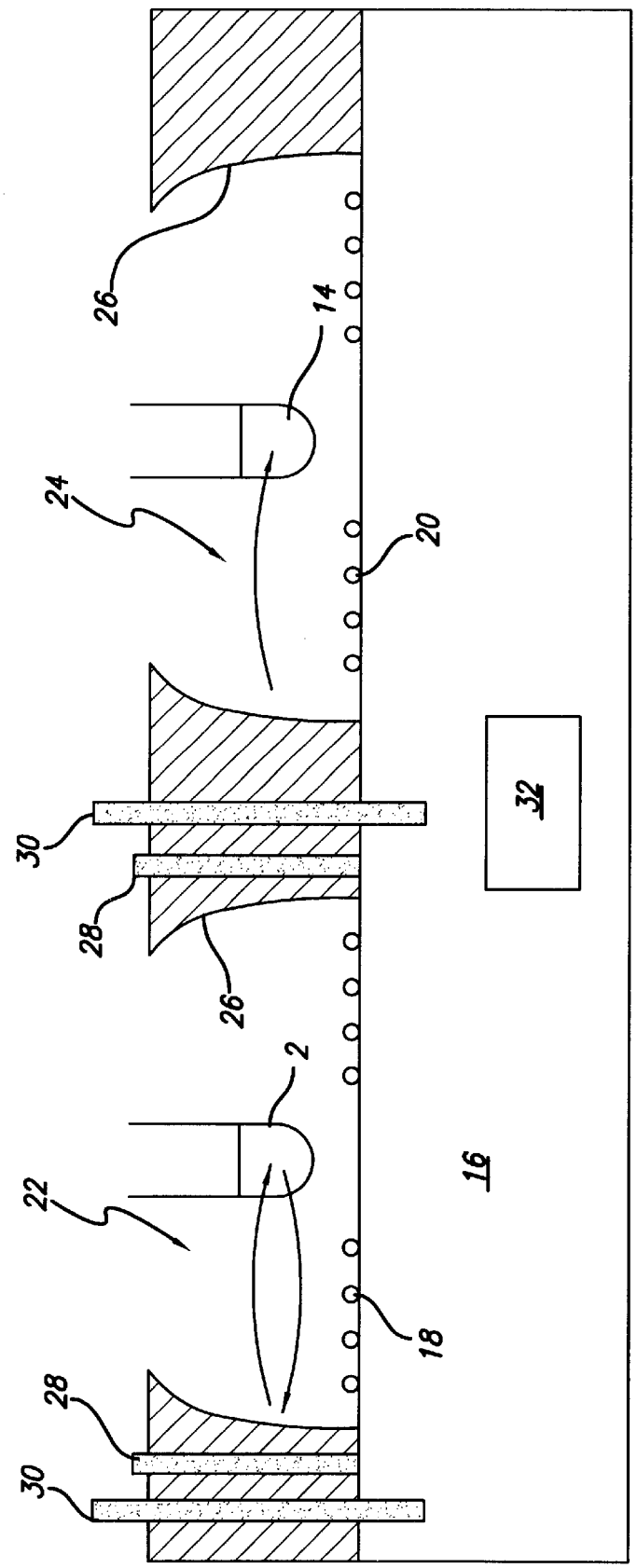
FIG. 4 a schematic representation of a fourth embodiment of the invention, by means of which the vibration pattern can be transferred from a transmitter substance or object to be activated to a carrier substance.
Figure 5:
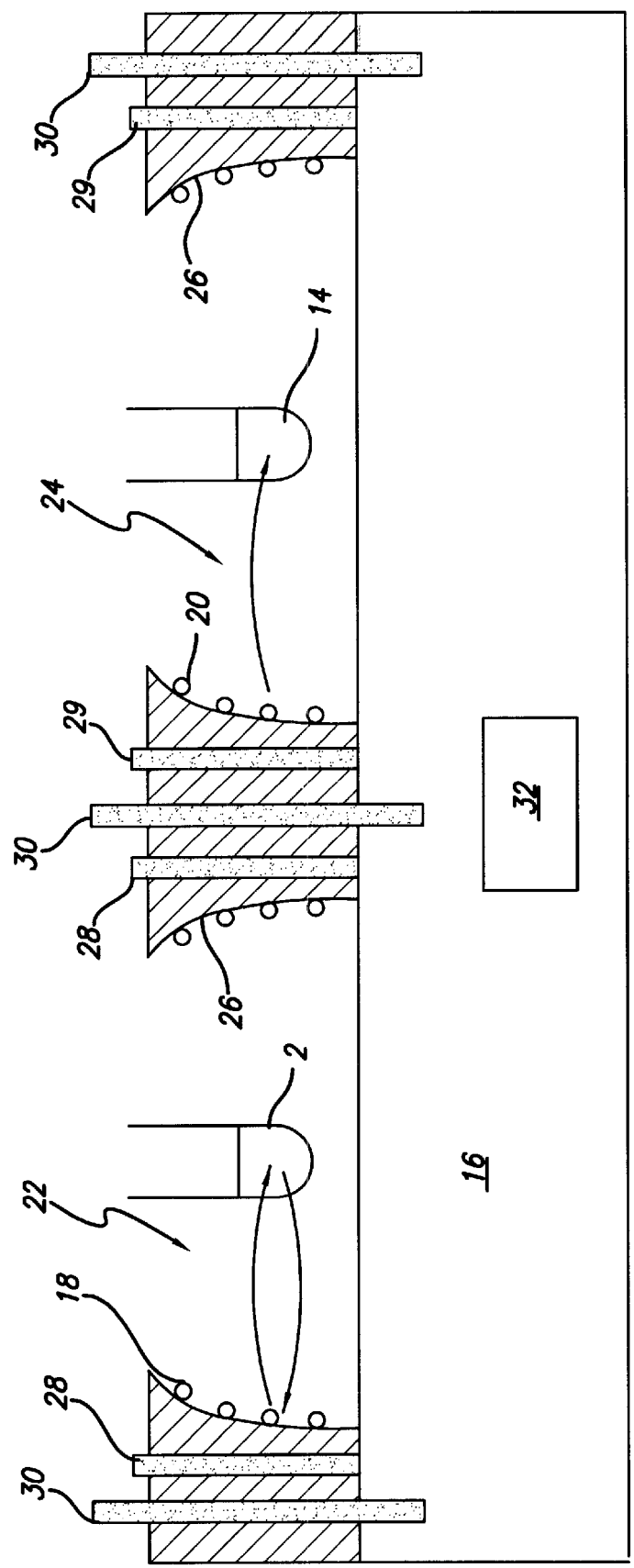
FIG. 5 a schematic representation of a fifth embodiment of the invention which is an adaptation of the fourth embodiment.

FIGS. 4 and 5 show a fourth and fifth embodiment of the invention, by means of which the vibration pattern from a transmitter substance 2 or an object to be activated is transferred to a carrier substance 14, in cross-section.

In the embodiment according to FIG. 4 the object to be activated or the transmitter substance 2 and the carrier substance 14 are each placed in a container 16 which is transparent to electromagnetic radiation over as wide a band as possible, and consists, for example, of quartz glass. An antenna 18 in the form of a spiral antenna is provided in the base section of container 16, below transmitter substance 2. The antenna 18 is used both as an activation antenna to activate transmitter substance 2 and also as a reception antenna to receive the signals arising from transmitter substance 2. A transmitter antenna 20 is arranged in the base section of container 16, below carrier substance 14, and this is also designed as a spiral antenna.

Transmitter substance 2 and carrier substance 14 are each introduced in beaker-shaped holders 22 and 24, the walls 26 of which are parabolic and narrow towards the top and form a reflector in order to produce reflections of the broad-band signal in the direction of the transmitter substance or carrier substance. Alternatively, the wall of the beaker may act as the antenna. Naturally, the curvature of walls 24 may also be designed to be other than parabolic. In the context of the invention, it has been found that it is advantageous if the antenna 18, 20 contain a curved reflector 24 by means of which the electromagnetic signals emitted by activating antenna 18 or transmitter antenna 20 are directed to transmitter substance 2 or carrier substance 14 or by means of which the electromagnetic signals emitted by transmitter substance 2 are collected for reception antenna 20. Signal transfer is improved in this way. Reflector 24 may consist, for example, of aluminium, steel or copper.

Holder 22 is surrounded by a first magnetic field coil 28, which in turn is surrounded by magnetic screening 30. Magnetic field coil 28 is used to produce a defined magnetic field, while magnetic screening 30 is used to compensate for or screen external magnetic fields.

The embodiment according to FIG. 5 differs from the embodiment according to FIG. 4 only in that the activation and reception antenna 18 and the transmitter antenna 20 are not in the base region of container 16 but are located on the relevant reflectors 26. In addition, holder 24 for carrier substance 14, in the same way as holder 22 for transmitter substance 2, is also surrounded by a second magnetic field coil 29 and passive magnetic screening 30. In this way, transfer of radiation to the carrier substance is possible under defined magnetic field conditions and overlapping with external magnetic fields is avoided.

Using magnetic field coils 28 and 29, a weak magnetic field of between 0 and 1 mT, preferably between 0 and 130 $\mu$T, can be produced in the region of transmitter substance 2.

Transmitter substance 2 may also be a living organism, human, animal or plant, or parts thereof.

What is claimed is:

1. A device for the controlled impact of objects in the form of substances, organic materials or living plant, animal or human bodies and parts thereof, comprising:

a facility for producing weak fixed or variable magnetic fields in the region of the object to be activated, and a facility for passive and/or active magnetic screening of external magnetic fields, in particular for screening the Earth's natural magnetic field.

2. The device according to claim 1, wherein at least one of a thermal, electromagnetic, electrical, optical or magnetic activating agent is located in the region of the object to be activated.

3. The device according to claim 2, further comprising:

a facility for holding a carrier substance, a transmitter antenna located in the region of carrier substance, a reception antenna located in the region of the object to be activated for receiving signals which arise from the object to be activated or from the activated object, and a processing unit linked to the reception antenna and the transmitter antenna for further processing of the signals received by the reception antenna and for transferring the further processed signals to the transmitter antenna.

4. The device according to claim 3, wherein the holder for the carrier substance contains passive or active magnetic screening.

5. The device according to claim 4, wherein the passive magnetic screening contains a layer made of a material with high permeability, in particular $\mu$-material or soft iron.

6. The device according to claim 5, wherein the material comprises $\mu$-material or soft iron.

7. The device according to claim 3, further comprising a facility for producing weak fixed or variable magnetic fields in the region of the carrier substance.

8. The device according to claim 7, wherein the facility for producing a weak magnetic field produces a magnetic field in the region between 0 and 1 mT and in particular between 0 and 130 $\mu$T.

9. The device according to claim 2, wherein the activating agent contains an activation antenna.

10. The device according to claim 9, wherein the reception antenna and the activation antenna are combined in one antenna.

11. The device according to claims 10, wherein one of the activation antenna, the reception antenna and the transmitter antenna further comprises a spiral antenna.

12. The device according to claim 11, wherein one of the activation antenna, the reception antenna and the sender antenna contains a curved reflector, whereby electromagnetic signals emitted by the activation antenna or the transmitter antenna are directed to the object to be activated or to the carrier substance or the electromagnetic signals emitted by the object to be activated are collected for the reception antenna.

13. The device according to claim 2, wherein the activation agent contains a light source.

14. The device according to claim 2, wherein the activating agent contains a heat source.

15. The device according to claim 2, wherein the activating agent can be activated, periodically or aperiodically, in a pulsed manner.

16. The device according to claim 2, wherein the activating agent emits in one of the atmospheric windows and/or is pulsed with a frequency in one of the atmospheric windows.

17. The device according to claim 3, wherein the activating agent is pulsed at a frequency of 7 to 8 Hz, preferably about 7.8 Hz.

18. The device according to claim 2, wherein the activating agent is pulsed at a frequency of about 7.8 Hz.

19. The device according to claim 1, wherein the strength and/or direction of the magnetic field can be changed with time by the facility for producing a weak magnetic field.

20. The device according to claim 1, wherein the screening facility comprises a facility for passive and/or active screening of Earth's magnetic field.

21. The device according to claim 1, wherein the facility for producing weak magnetic fields contains at least a control unit and a magnetic field coil, inside which is located the object to be activated, wherein the magnetic field coil is also used for active magnetic screening of the component of the Earth's natural magnetic field which runs parallel to the direction of the magnetic field inside the magnetic field coil.

22. The device according to claim 21, wherein at least one magnetic field coil is arranged in a container which is open on one face.

23. The device according to claim 21, wherein one of the control unit and the activating agent transmits a broad-band frequency spectrum.

24. The device according to claim 23, wherein the control unit further comprises a diode for transforming a transmitter signal into a broad-band spectrum containing high frequencies.

25. The device according to claim 24, wherein the control unit and processing unit further comprises means for suppressing or blanking out the activating signals.

26. A process for activating objects in the form of substances, organic materials or living plant bodies and parts thereof, the process steps:

screening of external magnetic fields, in particular the Earth's magnetic field, from the substance to be activated; and producing a weak fixed or varying magnetic field in the region of the substance to be activated.

27. The process according to claim 26, further comprising:

activating the object to be activated a thermal, electromagnetic, electrical, optical or magnetic activating agent.

28. The process according to claim 27, further comprising:

receiving signals arising from the object to be activated;

further processing these signals;

transferring the further processed signals to a carrier substance.

29. The process according to claim 28, further comprising:

screening the carrier substance from external magnetic fields, in particular from the Earth's magnetic field.

30. The process according to claim 28, further comprising:

producing a weak fixed or varying magnetic field in the region of the carrier substance.

31. The process according to claim 28, wherein the external magnetic fields comprise Earth's magnetic field.

32. The process according to claim 26, wherein the screening step comprises screening of Earth's magnetic field from the substance to be activated.

* * * * *